United States Patent [19]
Freed et al.

[11] Patent Number: 6,132,363
[45] Date of Patent: Oct. 17, 2000

[54] CARDIOVASCULAR SUPPORT CONTROL SYSTEM

[75] Inventors: Paul S. Freed, Bloomfield Hills; Michael Psakhis, Southfield; Paul G. DeDecker, Warren; Adrian Kantrowitz, Auburn Hills, all of Mich.

[73] Assignee: L.Vad Technology, Inc., Detroit, Mich.

[21] Appl. No.: 09/164,513

[22] Filed: Sep. 30, 1998

Related U.S. Application Data

[60] Provisional application No. 60/060,499, Sep. 30, 1997, and provisional application No. 60/097,819, Aug. 25, 1998.

[51] Int. Cl.$^7$ .............................. A61M 1/10; A61M 5/00
[52] U.S. Cl. ................................................ 600/16; 600/18
[58] Field of Search .......................................... 600/16–18

[56] References Cited

U.S. PATENT DOCUMENTS

| | | |
|---|---|---|
| 3,553,736 | 1/1971 | Kantrowitz et al. . |
| 3,585,983 | 6/1971 | Kantrowitz et al. . |
| 3,720,199 | 3/1973 | Rishton et al. . |
| 3,826,241 | 7/1974 | Bucalo . |
| 4,004,298 | 1/1977 | Freed . |
| 4,051,840 | 10/1977 | Kantrowitz et al. . |
| 4,077,394 | 3/1978 | MCCurdy . |
| 4,092,742 | 6/1978 | Kantrowitz et al. . |
| 4,321,914 | 3/1982 | Begovac et al. . |
| 4,393,873 | 7/1983 | Nawash et al. . |
| 4,527,549 | 7/1985 | Gabbay ................................... 128/1 D |
| 4,539,999 | 9/1985 | Mans . |
| 4,579,120 | 4/1986 | MacGregor . |
| 4,581,020 | 4/1986 | Mittleman . |
| 4,630,597 | 12/1986 | Kantrowitz et al. . |
| 4,634,422 | 1/1987 | Kantrowitz et al. . |
| 4,692,148 | 9/1987 | Kantrowitz et al. . |

(List continued on next page.)

OTHER PUBLICATIONS

Moore et al, "Microprocessor–based Controller for In–Series Cardiac Assistance", *Medical & Biological Engineering & Computing*, vol. 20, pp. 523–526, Jul. 1982.

Congestive Heart Failure, © 1994, Springer–Verlag, New York, Inc., Adrian Kantrowitz, Raul R. Cardona, John Au, and Paul S. Freed.

American Journal of Cardiology, © 1988, Intraaortic Balloon Pumping for Prolonged Circulatory Support, Paul S. Freed, MS, Tarik Wasfie, MD, Barina Zado, MD, and Adrian Kantrowitz, MD.

(List continued on next page.)

*Primary Examiner*—Carl H. Layno
*Attorney, Agent, or Firm*—Young & Basile, P.C.

[57] ABSTRACT

An apparatus for assisting cardiac function of a patient includes an inflatable chamber operably positionable with respect to an aorta of the patient, a percutaneous access device implantable with respect to a hypogastric region of the patient and connectible in fluid communication with the inflatable chamber, and a drive unit connectible through the percutaneous access device for selectively inflating and deflating the inflatable chamber in accordance with a control program stored in memory. The control program controls the drive unit in response to a periodically scheduled patient monitoring routine for measuring values of the physiology of the patient. The control program uses measured values as modified in accordance with the control program and physician programmable parameters for assisting cardiac function of the patient. The program includes the steps of automatically controlling the drive unit in response to a periodically scheduled patient monitoring routine for measuring values of physiology of the patient, and using measured values as modified in accordance with physician programmable parameters for assisting cardiac function of the patient. A software program is connectible in electronic communication with the control program for adjusting settings of the drive unit. The software program is capable of one or more of the following functions: retrieving current values of physician programmable parameters, selectively retrieving a history of the drive unit operation including error detection records, displaying a continuous ECG, and/or displaying a single-beat sample of aortic pressure waveform obtained in real time from the patient.

20 Claims, 4 Drawing Sheets

U.S. PATENT DOCUMENTS

| | | |
|---|---|---|
| 4,712,563 | 12/1987 | Link . |
| 4,733,652 | 3/1988 | Kantrowitz et al. . |
| 4,741,328 | 5/1988 | Gabbay . |
| 4,774,960 | 10/1988 | Arnold et al. . |
| 4,781,715 | 11/1988 | Wurzel . |
| 4,782,817 | 11/1988 | Singh et al. . |
| 4,785,795 | 11/1988 | Singh . |
| 4,790,826 | 12/1988 | Elftman . |
| 4,804,369 | 2/1989 | Lapeyre et al. . |
| 4,809,681 | 3/1989 | Kantrowitz et al. . |
| 4,810,246 | 3/1989 | Frisch et al. . |
| 4,877,035 | 10/1989 | Bogen et al. ............ 600/485 |
| 4,888,011 | 12/1989 | Kung et al. . |
| 4,897,081 | 1/1990 | Poirier et al. . |
| 4,902,272 | 2/1990 | Milder et al. . |
| 4,913,700 | 4/1990 | Kantrowitz et al. . |
| 4,955,861 | 9/1990 | Enegren et al. . |
| 4,974,774 | 12/1990 | Nakagawa et al. . |
| 5,045,051 | 9/1991 | Milder et al. . |
| 5,089,016 | 2/1992 | Millner et al. . |
| 5,098,397 | 3/1992 | Svensson et al. . |
| 5,135,488 | 8/1992 | Foote et al. . |
| 5,139,508 | 8/1992 | Kantrowitz et al. . |
| 5,169,379 | 12/1992 | Freed et al. . |
| 5,201,755 | 4/1993 | Klement . |
| 5,219,326 | 6/1993 | Hattler . |
| 5,242,374 | 9/1993 | Isoyama et al. . |
| 5,242,415 | 9/1993 | Kantrowitz et al. . |
| 5,312,364 | 5/1994 | Jacobs . |
| 5,336,167 | 8/1994 | Sullivan et al. . |
| 5,352,180 | 10/1994 | Candelon et al. . |
| 5,356,378 | 10/1994 | Doan . |
| 5,372,709 | 12/1994 | Hood . |
| 5,387,192 | 2/1995 | Glantz et al. . |
| 5,411,027 | 5/1995 | Wiklund et al. ............ 600/18 |
| 5,423,746 | 6/1995 | Burkett et al. . |
| 5,445,622 | 8/1995 | Brown . |
| 5,482,446 | 1/1996 | Williamson et al. . |
| 5,514,079 | 5/1996 | Dillon . |
| 5,637,088 | 6/1997 | Wenner et al. . |
| 5,713,954 | 2/1998 | Rosenberg et al. ............ 623/3 |
| 5,833,619 | 11/1998 | Freed et al. ............ 600/485 |
| 5,833,655 | 11/1998 | Freed et al. . |
| 5,904,666 | 5/1999 | DeDecker et al. . |
| 6,042,532 | 3/2000 | Freed et al. . |

OTHER PUBLICATIONS

Surgery, © 1969, A Dynamic Aortic Patch as a Permanent Mechanical Auxiliary Ventricle: Experimental Studies, Eduard Sujansky, M.D., Steinar Tjonneland, M.D., Paul S. Freed, M.S., Adrian Kantrowitz, M.D.

Transplantation Proceedings, ©1971, Current Status of Intraaortic Balloon Pump and Initial Clinical Experience With Aortic Patch Mechanical Auxiliary Ventricle, Adrian Kantrowitz, Joseph S. Krakauer, George Zorzi, Melvyn Rubenfire, Paul S. Freed, Steven Phillips, Marc Lipsius, Claudio Titone, Philip Cascade, and Dov Jaron.

Journal of Biomedical Materials Research, © 1978, Biocompatibility Tests of Components of an Implantable Cardiac Assist Device, Andreas F. Von Recum, Hiroji Imamura, Paul S. Freed, Adrian Kantrowitz, Shan–Te Chen, Merlin E. Ekstrom, Charles A. Baechler and Marion I. Barnhart.

Trans. Amer. Soc. Artif. Int. Organs, © 1972, Initial Clinical Experience with a New Permanent Mechanical Auxiliary Ventricle: The Dynamic Aortic Patch, Adrian Kantrowitz, J. Krakauer, M. Rubenfire, D. Jaron, P. S. Freed, W. Welkowitz, P. Cascade, W. J. Wajszczuk, M. Lipsius, M. Ciborski, S. J. Phillips, and M. T. Hayden.

American Journal of Nursing, © 1973, Care of a Man with a Partial Artificial Heart, Roberta Nelson, Judy Smith, Ruth Drummond, Hilde Pollard Joyce Billingsley, Miriam Nikkila.

CARDIOVASCULAR SUPPORT CONTROL SYSTEM

RELATED APPLICATIONS

This application is a continuation of U.S. Provisional Application Ser. Nos. 60/060,499 filed Sep. 30, 1997 and 60/097,819 filed Aug. 25, 1998.

FIELD OF THE INVENTION

The invention relates to a pressure control system for a cardiac assist device.

BACKGROUND OF THE INVENTION

Congestive heart failure is one of the major causes of mortality and morbidity in the United States, affecting more than 2 million Americans. Pharmacologic therapy has prolonged survival and improved the quality of life for many patients. For cardiac patients who do not respond to conventional treatments, heart transplantation is an effective treatment. However, the shortage of donor hearts limits its application. Mechanical assistance—in the form of the intraaortic balloon pump (IABP)—has become commonplace for the treatment of acute heart failure. But to date, no forms of mechanical assistance for chronic heart failure (CHF) are commercially available.

During the last decade, left ventricular assist (LVA) systems have been used as a bridge to a heart transplant. These systems take over all the work of the heart and have been used for more than a year in many patients who have then gone on to be transplanted. The success of this prolonged cardiac support has led to ongoing clinical trials to evaluate the use of LVA systems as an alternative to medical treatment.

SUMMARY OF THE INVENTION

The system is designed for use in selected patients with advanced chronic congestive failure no longer responsive to pharmacologic management. Like the intraaortic balloon pump (IABP), the present invention is a left ventricular assist (LVA) system that provides diastolic augmentation to the failing left ventricle. However, the present invention differs from the IABP in a number of respects. The present invention is intended to remain in the body indefinitely, providing long-term cardiac support as an alternative to medical treatment. It is not a bridge to a heart transplant. Patients will be discharged from the hospital, live at home, and resume many normal activities.

The system consists of: the blood pump, an inflatable bladder sutured into the wall of the descending thoracic aorta, the percutaneous access device (PAD), a through-the-skin port that allows power and electrical signals to pass between the drive unit and the blood pump, and the external drive unit, which powers and controls the blood pump.

The blood pump has only one moving part—a diaphragm—and no valves. The pump has a stroke volume of up to 60 cc. To inflate the blood pump, pressurized room air is supplied from a wearable (<5 lb.) battery-powered unit or a larger drive unit powered by household electricity. The air reaches the blood pump through an external drive line, attached to the drive unit, and an internal drive line implanted in the patient. The internal and external drive lines connect to each other through the percutaneous access device. The PAD also serves as a conduit for electrical signals that are transmitted from the heart to the drive unit through electrical leads.

Like the intraaortic balloon pump (IABP), a device whose effectiveness in providing circulatory support for days to months is well accepted, the present invention operates on the principle of diastolic augmentation. The system inflates the blood pump during diastole and deflates it just before systole. When deflated, the pump conforms to the inner wall of the aorta, functioning as a passive aortic graft.

In a patient with left ventricular failure, diastolic augmentation reduces left ventricular afterload and improves coronary perfusion. This leads to improved myocardial oxygen supply and demand balance. While the system takes advantage of the same operating principle and anatomic location as the IABP, the larger stroke volume of the present invention is expected to yield improved hemodynamic benefits. Unlike the IABP, which is designed for short-term, in-hospital treatment, the present invention is designed for long-term circulatory support of the CHF patient who will return home after recovering from implant surgery.

During the last decade, left ventricular assist (LVA) systems have been used as a bridge to a heart transplant. These systems are designed to take over all of the work of the left ventricle. In contrast, the present invention requires that patients have some functioning myocardium and can benefit from diastolic augmentation. Several features set the system apart from other LVA systems designed for long-term support:

It is an "on demand" system. The present invention can provide either continuous or intermittent cardiac support, according to the physician's determination of the patient's needs. When the system is turned off, the patient does not need to be connected to the machine. Because other LVA systems are designed with valves, they must operate continuously to avoid the pooling of blood, which leads to thrombosis and emboli. The present invention can operate intermittently because it has no valves. Long-term tests of the present invention and its predecessors indicate that turning the assist device on after it has been off for some time does not result in emboli.

Patients will not be on anticoagulant therapy. The blood-contacting surface of the present invention is textured to encourage tissue in growth. Its biocompatibility has been confirmed in calf studies in which the blood pump was activated intermittently for periods up to 25 months. No surgical alteration of cardiac anatomy is necessary, so no functioning myocardium is removed when the present invention is implanted.

Following the success of LVA systems as a "bridge to transplant" in the past decade, trials are underway to evaluate these systems for long-term use as an alternative to medical treatment in CHF. A number of cardiomyopathy patients have recovered sufficiently to be removed from the transplant list and to have the LVA system removed. LVA systems are therefore also becoming known as a "bridge to recovery." The present invention is not a direct competitor of these LVA systems. Rather, it is one of a family of mechanical support devices, each designed for particular patient needs. In the future, physicians will be able to choose from various models to provide the best match for each patient.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

At the start of the noninvasive screening process, a skin biopsy will be taken and cells cultured onto the implantable part of the PAD. In cell culture, the patient's fibroblasts extend cell processes into the nanoporous PAD neck. Soon after PAD implantation, host fibroblasts form a meshlike, collagenous structure with the fibroblasts that already have coated the neck. This creates a biological seal which inhibits penetration by infectious organisms.

About one week before the implantation of the blood pump, the PAD will be implanted. In this surgical procedure, a transverse skin incision is made at the level of $L_{1-2}$ of the left hypogastric region. From this incision a subcutaneous pocket 10 cm in diameter is created, and a circular incision is made in the skin covering the pocket. The PAD is inserted through the transverse incision into the subcutaneous pocket and exposed through the circular incision. Care is taken to avoid contact with the PAD fibroblast coating. The pocket is closed using Prolene sutures.

During the healing process, the PAD becomes stabilized by scar tissue. It is essential, therefore, to minimize movement of the PAD site after insertion.

Before induction of anesthesia, ECG, IV lines and a urinary catheter will be introduced. Angiographic catheters will be inserted in the right radial artery and left femoral artery for proximal and distal arterial pressure monitoring. The patient will be induced and intubated. Anesthesia will be maintained via inhalant anesthetic (Isoflurane). A Swan-Ganz catheter will be inserted via the left jugular vein and passed into the pulmonary artery for monitoring PAP, PCWP, CO, and CVP. Blood gases, Hb, ACT, and Hct will be monitored during surgery.

The blood pump will be inserted through a left thoracotomy approach. Following heparinization, the patient will be placed on coronary artery bypass. The aorta will be cross clamped above and below the intended implant site using a staged technique. With the help of a template, a longitudinal incision will be made in the anterior aortic wall. The blood pump will then be sutured to the edges of the opening created by the incision and the cross clamps removed.

Figure 1:
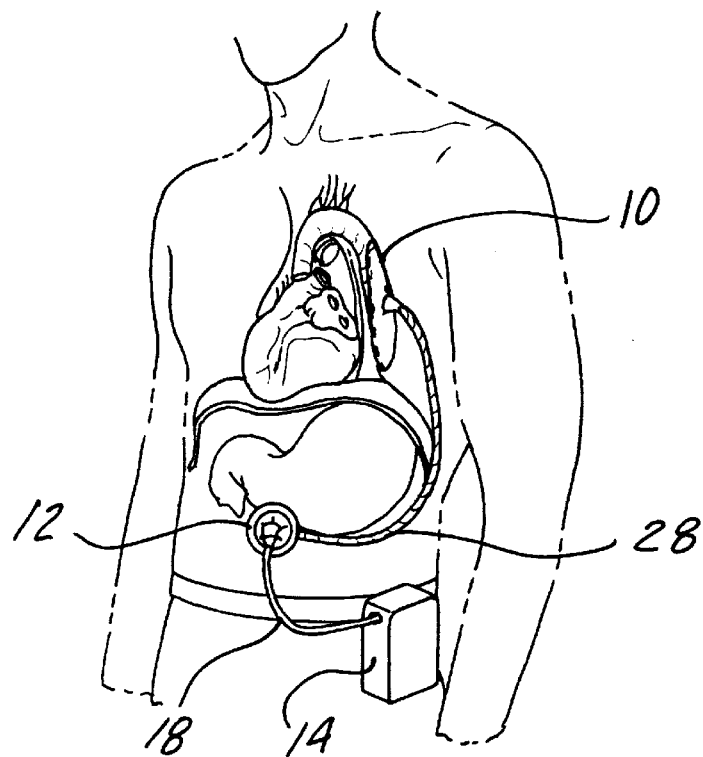
FIG. 1 illustrates the system according to the present invention includes the blood pump, the PAD, and the drive unit.

The drive unit will be temporarily connected to the blood pump to verify that the pumping membrane is intact and has not been damaged during insertion. Any suture line leaks or discontinuities will be repaired. The patient will be weaned from bypass and heparinization will be reversed with Protamine. Two pacing electrodes will be placed on the epicardium of the left ventricle. With the help of a tunneling device, the internal drive line will be brought from the thoracic cavity to the PAD. Through a separate tunnel the pacing electrodes will be passed from the pocket to the thoracic cavity and attached to the ends of the blood pump. The blood pump will be reconnected to the drive unit through the PAD. Two chest tubes will be placed into the thoracic cavity, one anterior and one posterior and connected to an underwater seal. The thoracic cavity will then be closed in layers. The complete system is shown in FIG. 1.

Figure 2:
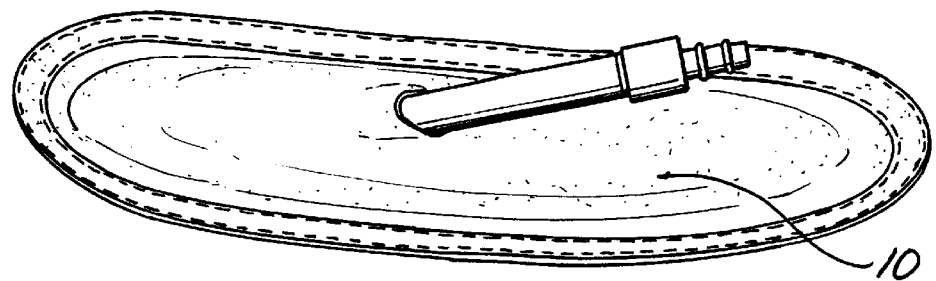
FIG. 2 illustrates the blood pump.

The blood pump 10 is an approximately 6.5-inch long polyurethane bladder illustrated in FIG. 2 and is sutured to the edges of an incision of matched size in the wall of the descending thoracic aorta. The pump is inflated with filtered room air supplied from the drive unit. The blood pump can be adjusted for full or partial inflation.

The internal drive line is a kink resistant, 5 mm ID tube that extends from the implanted blood pump to the PAD 12. It provides a pneumatic connection between the blood pump and the PAD.

Two standard pacemaker leads are implanted in the patient's epicardium during the blood pump implantation and brought through a subcutaneous tunnel to the PAD. These leads sense the electrocardiogram and conduct it to the drive unit, which processes the signal to identify the R wave. The R wave triggers inflation and deflation of the blood pump.

Figure 3:
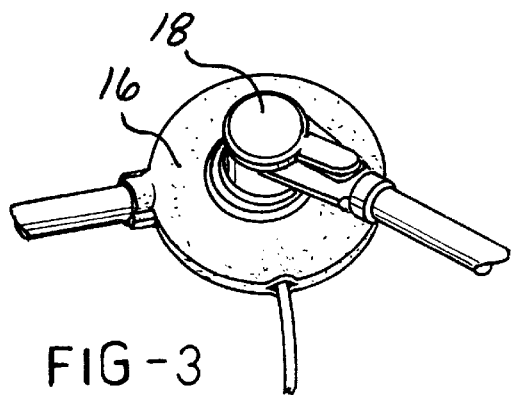
FIG. 3 illustrates parts of the percutaneous access device (PAD) according to the present invention.

The PAD has two main parts as illustrated in FIG. 3: (1) an implanted, 0.75" diameter cylindrical neck with a flexible, cloth-covered flange at a base 16, precoated with fibroblasts and implanted about a week before blood pump insertion, and positioned near the patient's navel, with the flange under the skin, and inside the neck is a replaceable turret; and (2) an external, detachable part 18 which connects the PAD to the drive unit 14.

Patients can be provided with two drive units: (1) the Line-powered Drive Unit (LPDU) operates continuously on household current, has backup batteries capable of nearly 3-hour service, is intended mainly for use when the patient is stationary, either seated or lying, and is housed in a wheeled suitcase; and (2) the Wearable Drive Unit (WDU) is intended to be used once or twice daily, not for continuous use, can run nearly 2 hours on one set of batteries, allows the patient to move freely while receiving cardiac support, and can be worn or carried away from home for standby use.

Both drive units control blood pump inflation and deflation timing and automatically adjust the timing for changes in heart rate. The units can be programmed, under a physician's direction, to tailor blood pump operation to each patient's cardiac function. This is done via PC-based software.

Safety features are built into each drive unit to protect the patient if the system fails. For example, the drive unit's motor and valves will shut down in case of a software failure. When this happens, the blood pump deflates and remains safely deflated. To make sure that the WDU does not operate erratically when its batteries get low, the system monitors battery voltage. When voltage drops below a certain level, the system makes sure the valves and motor are in a safe state and then shuts itself down. The LPDU is capable of detecting a pinhole leak in the blood pump should one develop. The WDU is not. For this reason, the LPDU should be used most of the time and the WDU only occasionally and for short periods.

The drive unit (either the LPDU or the WDU) automatically adjusts blood pump inflation and deflation timing based on: (1) comparison of the duration of any R—R interval (except the first) with its predecessors; (2) periodic aortic pressure measurement; (3) determination of the Q-S$_2$ interval; and (4) application of an Inflation Adjustment factor, defined by the physician.

In addition, a number of parameters can be programmed according to the physician's directions. Each of the programmable parameters has a default setting, stored in the drive unit's Patient Parameter Table (PPT) (See Table 1). These settings can be modified to obtain the maximum benefits of diastolic augmentation for a given patient. Each of the programmable parameters is discussed in further detail below.

Changes in the patient's clinical status or medications can affect LV contractility, coronary artery blood flow, and LV end-diastolic volume and pressure. These changes may, in turn, affect the timing of inflation and deflation. Therefore, any change in medications or significant change in clinical status requires a reassessment of the PPT settings.

The same software program that is used to adjust the drive unit settings can also retrieve the current PPT settings and a history of the unit's operation. The software also can display a continuous ECG and single-beat samples of aortic pressure waveforms obtained in real time from the patient.

at the end of diastole. Once the intra-arterial catheter is removed, it will no longer be possible to base timing adjustments on direct arterial pressure waveform measurements. For that reason, pressure waveform data must be recorded over a range of heart rates and physiological conditions while the catheter is in place. These data will serve as a guide for future timing adjustments, after the catheter has been removed. Additional reference measurements should be made any time an intra-arterial catheter is placed subsequently, such as during a cardiac catheterization.

As discussed above, blood pump inflation timing is determined by Q-S$_2$ and the Inflation Adjustment setting programmed into the drive unit. If Q-S$_2$ changes, the previously programmed Inflation Adjustment setting may no longer be appropriate, and the physician must adjust it. Reference timing data gathered when the patient had an indwelling arterial catheter should be used as a guide in making new Inflation Adjustment settings.

In adjusting settings, the physician must consider that: (1) the Q-S$_2$ interval will change, depending on whether the measured cardiac cycle is assisted, unassisted for a few beats, or unassisted for more than a few beats (the partial cycle measurement can be obtained only from an unassisted

TABLE 1

Summary of Patient Parameters

| PARAMETER | UNITS | MINIMUM | DEFAULT | MAXIMUM |
| --- | --- | --- | --- | --- |
| Scheduled Pressure Measurement | min | 3 | 10 | 20 |
| Pressure Measurement Lock-Out | sec | 15 | 30 | 60 |
| NSR Deviation | % | 10 | 20 | 80 |
| Inflation Adjustment | msec* | 0 | 28 | 50 |
| Deflation Adjustment | msec* | 0 | 0 | 80 |
| Arrhythmia Threshold | % | 5 | 10 | 15 |
| Arrhythmia Inflate Delay | msec* | 250 | 400 | 420 |
| Dicrotic Notch Earliest (DNE) | msec* | 150 | 180 | 200 |
| Dicrotic Notch Latest (DNL) | msec* | 300 | 350 | 420 |
| Dicrotic Notch Default | msec* | DNE entry | 300 | DNL entry |
| Filling Time | msec* | 60 | 128 | 160 |
| Stroke Volume | % | 25 | 100 | 110 |

Periodically, the drive unit interrupts counterpulsation for two cardiac cycles to obtain an aortic pressure waveform from which the Q-S$_2$ interval is measured. This method of measuring and processing the central aortic pressure is called a partial cycle. The drive unit uses the measurement to adjust inflation timing of the blood pump, as the heart rate and hemodynamic state of the patient changes. The timing is always further modified by the Inflation Adjustment value, which is specified by the physician. The interval between Q-S$_2$ measurements is based on the NSR Deviation, a programmable value that represents percentage changes in heart rate. However, the physician can prescribe the maximum and minimum intervals between measurements by adjusting the Scheduled Pressure Measurement and Pressure Measurement Lock-Out settings. The Scheduled Pressure Measurement setting determines the maximum time between measurements. The Pressure Measurement Lock-Out setting controls the minimum time between measurements.

As long as an intra-arterial catheter is in place, the drive unit operator must ascertain the patient's arterial pressure waveform and manually change inflation and deflation adjustment settings until the desired assist waveform is obtained. For example, the blood pump might be set to begin inflating just after the dicrotic notch and to begin deflating beat that follows an assisted beat); (2) the patient receives no hemodynamic support during the partial cycle; and (3) the patient must be in normal sinus rhythm immediately preceding partial cycle measurements. If the patient is not in stable sinus rhythm, aortic pressure will not be measured during the partial cycle, and the drive unit will base timing on a programmable value, the Arrhythmia Inflate Delay.

The frequency with which partial cycle measurements are made is a matter of clinical judgment. Frequent measurement allows better tracking of changes in the patient's condition, but the cost is two cardiac cycles during which the patient receives no left ventricular assistance.

At every beat, the drive unit calculates the percentage change between the current R—R interval and the R—R interval measured in the previous partial cycle. The percentage change is the NSR (Normal Sinus Rhythm). If the NSR exceeds the NSR Deviation value prescribed by the physician, the drive unit makes a new partial cycle measurement.

Ejection time of an unassisted cardiac cycle is longer than that of an assisted cardiac cycle. Inflation Adjustment is a physician-determined time interval added to Q-S$_2$ to compensate for that phenomenon. The Inflation Adjustment setting also allows adjustments to be made for mechanical factors that affect timing.

The default setting of the Inflation Adjustment causes blood pump inflation to begin at the predicted time of appearance of the dicrotic notch, based on the most recently measured $Q-S_2$. A negative Inflation Adjustment value causes blood pump inflation to start a specific amount of time before the predicted occurrence of the dicrotic notch. Conversely, a positive Inflation Adjustment value delays blood pump inflation a specific amount of time after the predicted occurrence of the dicrotic notch.

If the decision about Inflation Adjustment settings is being based on reference data collected when the patient's physiologic/clinical status was different, the physician must consider how the patient's current clinical status will affect optimal timing adjustments. If the Inflation Adjustment setting delays blood pump inflation too long after the dicrotic notch, suboptimal coronary perfusion results. Conversely, early blood pump inflation could lead to premature aortic valve closure and/or aortic regurgitation with resultant reduction in LV stroke volume. The physician must determine the risk-benefit ratio of the inflation adjustment for a patient at any given time in the patient's clinical course.

The Deflation Adjustment parameter sets the time interval between detection of the upstroke of the R wave and initiation of blood pump deflation. If the Deflation Adjustment setting is at its default value of zero, the blood pump will deflate 20–30 msec before the QRS. Increasing the Deflation Adjustment value delays deflation, thereby prolonging the period of blood pump inflation.

Like Inflation Adjustment, the Deflation Adjustment setting should be altered only on the basis of the patient's reference data. Premature deflation may reduce coronary artery blood flow. Late deflation may result in suboptimal reduction in left ventricular afterload. The physician must determine the risk-benefit ratio of deflation timing adjustments.

During any arrhythmia, the partial cycle measurement has little predictive value. Therefore, when the drive unit senses an arrhythmia, it suspends partial cycle measurements for 15–60 seconds. During this period, it bases timing on a physician-selected value (the Arrhythmia Inflate Delay value) instead of on the $Q-S_2$ interval.

The Arrhythmia Threshold setting allows the physician to adjust the drive unit's "sensitivity" to arrhythmias. To determine if there is an arrhythmia, the drive unit calculates an arrhythmia index for each cardiac cycle. The arrhythmia index is defined as: (average D over n beats (R—R)/average R—R over n beats) 100%, where n is 8 or 16 beats, D=absolute change, and (R—R)=measured R—R interval. If the result exceeds the Arrhythmia Threshold setting selected by the physician, the drive unit switches to a default mode. In default mode, the following conditions exist:
(1) The Deflation Adjustment is set to zero. In this state, the blood pump will automatically deflate whenever it senses the upstroke of the R wave.
(2) The Arrhythmia Inflate Delay replaces the $Q-S_2$ interval.
(3) The Inflation Adjustment is added to the Arrhythmia Inflate Delay.

The above default settings result in early deflation and late inflation of the blood pump. These timing settings are conservative in order to minimize chances of adverse events. The conditions defined by the arrhythmia default mode will continue for as long as the physician has specified with the Pressure Measurement Lock-Out setting.

As discussed above, the drive unit replaces the measured $Q-S_2$ interval with the Arrhythmia Inflate Delay value when it senses an arrhythmia. In effect, the Arrhythmia Inflate Delay functions as a default $Q-S_2$. Under these conditions, the Inflation Adjustment setting remains in effect. The Arrhythmia Inflate Delay value should be selected on the basis of the patient's arrhythmia history. If the patient has any persistent arrhythmia, a pacemaker should be considered, as it will allow more effective LV assistance.

To detect the dicrotic notch, the drive unit uses an algorithm that inspects the aortic pressure waveform, within a physician-prescribed time window. If a dicrotic notch is not detected within this window, the algorithm uses a physician-prescribed default value for the location of the dicrotic notch.

The window is defined by a beginning point (Dicrotic Notch Earliest, or DNE) and an end point (Dicrotic Notch Latest, or DNL). The physician sets both values in reference to the onset of the R wave. The physician also sets a default value, the Dicrotic Notch Default, to be used if the algorithm cannot locate a dicrotic notch within the prescribed window. All three above parameters must be coordinated. That is, the DNE value must be less than the DNL value, and the default value must lie between the DNE and the DNL values.

The algorithm may mistake an artifact for the dicrotic notch. Making the window narrow decreases the likelihood of this happening. But if the window is too narrow and does not include the dicrotic notch, the drive unit will use the default setting, rather than the actual dicrotic notch. Conversely, making the window wider allows tracking the dicrotic notch over a wider range of heart rates, but also increases the likelihood of mistaking an artifact for the notch. To find out if the algorithm is using the actual dicrotic notch, an artifact, or the default setting, use the PC-based software.

The size of the window should also reflect variations in the patient's $Q-S_2$ over time and over different hemodynamic conditions.

The Filling Time setting establishes a target value for the rate of blood pump inflation. However, it is recommended that the default value be used. The default value takes into account numerous constraints that are necessary to maintain appropriate and safe pressure gradients. In practice, these constraints have priority over meeting the Filling Time target value.

Over-inflating the blood pump may shorten its lifespan. Therefore, there are built-in limitations to the pressure and stroke volume that can be delivered to the blood pump. A Stroke Volume setting of 100% delivers a stroke volume of 50–55 cc. The Stroke Volume can be adjusted to deliver from 25% to 110% of full stroke volume. It is recommended that stroke volume not exceed 100% for more than 2–3 days. Note that such a setting may require a change in the Assist Pressure Correction Factor.

Blood pump stroke volume should not exceed the LV stroke volume. If blood pump stroke volume is set higher than LV stroke volume, and if deflation is well-timed, then blood pump deflation may "steal" blood from the coronary and other arteries.

In the immediate post-operative period (2 weeks), stroke volume should be set no higher than 60% to reduce peak assisted pressure and resulting stress on the fresh suture line. After the sutures have stabilized, stroke volume may be increased.

The system detects pacemaker spikes and rejects them as QRS complexes. In addition, over a course of 16 cardiac cycles, the system learns the shape and size of the tail that follows the pacemaker spike and subtracts it from the ECG signal. This allows for better detection of the QRS complex when the tail and the real QRS are superimposed. However, if the patient has a dual chamber pacemaker, the algorithm will average the two potentially significantly different tails. This may confuse the pacemaker detection algorithm and may require reprogramming of the pacemaker.

Two alarms warn of excessive pressure in the blood pump. One alarm is activated whenever pressure in the drive line reaches 260 mm Hg. The second alarm is programmable. It is activated when the pressure in the drive line exceeds systolic blood pressure by an amount the physician has selected. If this alarm is set at its default value of zero, the alarm threshold is 80 mm Hg above systolic pressure. By adjusting the Assist Pressure Correction Factor, the alarm threshold may be increased by up to 50 mm Hg or lowered by as much as 20 mm Hg, resulting in thresholds of 60 to 130 mm Hg above systolic pressure.

In general, the threshold should be as low as possible, without causing false alarms or interfering with good pumping. The threshold can be increased if the unassisted peak systolic pressure is low or if the blood pump is being operated above the 100% Stroke Volume setting. Under these conditions, the difference between systolic pressure and pump pressure will be sufficient to activate the alarm unless the threshold has been increased. The default setting is appropriate in most other situations.

Closed-chest defibrillation poses no risks to the blood pump. If CPR must be performed within the first few days after surgery, damage to the suture line is possible. During this same period, any medication that increases systemic blood pressure to an abnormally high level may also disrupt the suture line. The augmented blood pressure during these few days should be at the lowest level compatible with the patient's well being, so as not to risk disrupting the suture line.

Counterpulsation should be temporarily suspended during CPR because of the inherent inability to synchronize the assist device to chest compression. However, as soon as a rhythm is re-established and counterpulsation with correct timing can be implemented, the blood pump should be restarted.

Despite the difficult conditions of resuscitation, personnel should attempt, if possible, to prevent mechanical stress to the percutaneous access device, as this could result in disruption of the access device tissue adhesion and lead to infection.

Figure 4:
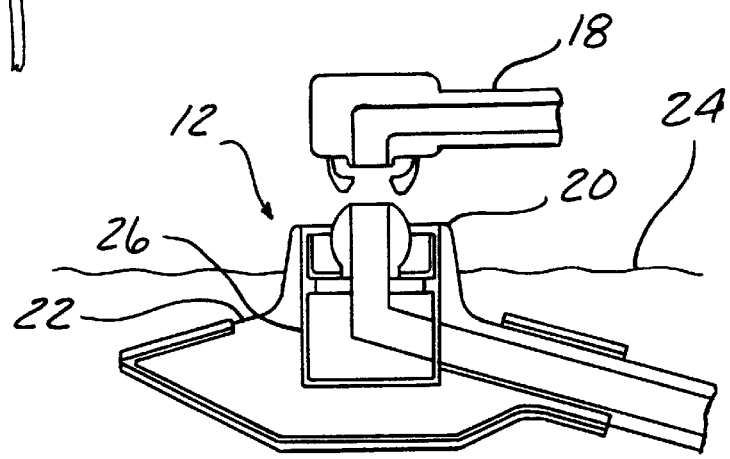
FIG. 4 illustrates the PAD as implanted through the skin.
Figure 5:
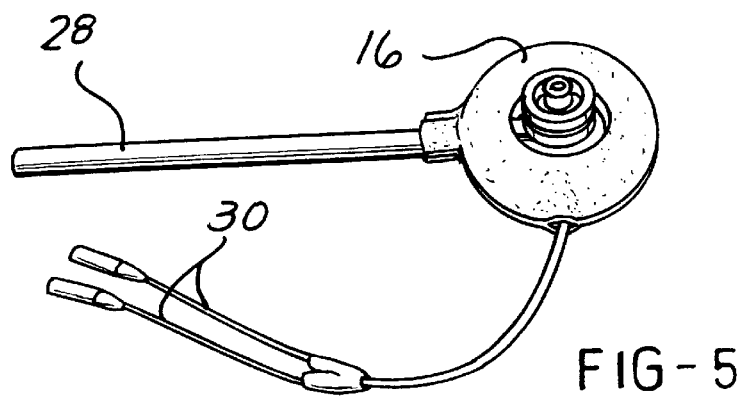
FIG. 5 illustrates the implanted part of the percutaneous access device with the internal drive line and pacing leads attached to the three terminals at the left.

Recall that the PAD 12 has three main parts as illustrated in FIG. 4: (1) a cylindrical neck 20 with a flange 22 at the bottom, implanted so that the neck protrudes through the skin 24; (2) a replaceable turret 26 inside the neck; and (3) an external part 18, which connects to the drive unit's external drive line. The PAD is positioned near the patient's navel. During the implantation procedure, an internal drive line 28 from the blood pump and the pacemaker leads 30 from the epicardium are connected to the implanted part of the PAD as illustrated prior to implantation in FIG. 5.

Figure 6:
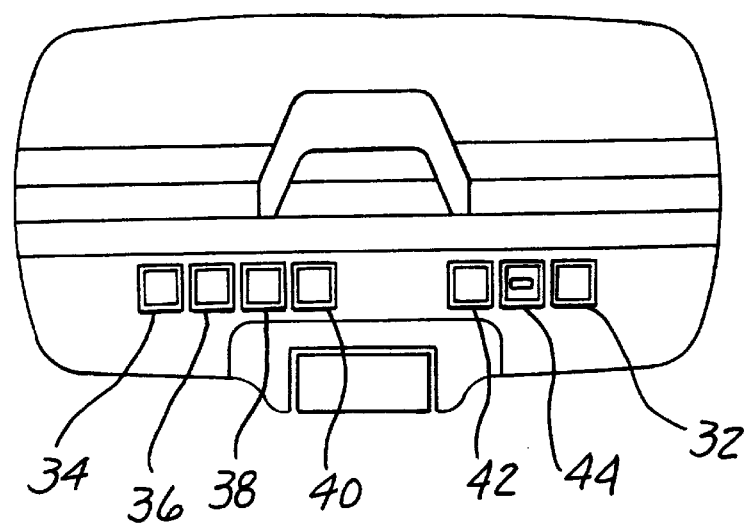
FIG. 6 illustrates a diagram of the line-powered drive unit (LPDU) showing positions of switches, and indicator lights.

The LPDU is housed in a wheeled suitcase with a retractable handle and a top view is illustrated in FIG. 6. It uses household current (110-volt AC). It also contains backup batteries for short-term operation in case of a power failure. Attached to the suitcase is a pouch where the external drive line can be stored when not in use. When the external drive line is stored in the pouch, the PAD connector should be snapped onto the ball inside the pouch. Instructions can also be stored in the pouch.

The LPDU is designed to be used mainly when the patient is resting in a chair or bed. The physician may allow the patient to walk a short distance, wheeling the LPDU on a hard, level surface. The LPDU has seven indicator lights, shown in FIG. 6. The blue "AC ON/OFF" switch 32 turns on power to the drive unit, but it does not activate pumping. The green "PUMP ON/OFF" switch 34 must be pressed to start the pumping process. The orange "BATTERY LOW" light 36, red "CHECK CONNECTION" light 38, and red "REPLACE DRIVE" light 40, along with different patterns of beeps, alert the user to problems. The charge level of the LPDU's built-in backup batteries is tested by pressing the orange "BATTERY STATUS" button 42 while the "AC ON/OFF" button is in the "OFF" position. If all five of the orange "BATTERY LEVEL" lights 44 come on, the batteries are fully charged. The LPDU also has a light inside the plug at the end of its power cord. The light glows when the cord is plugged into a live outlet.

The present invention includes software for use in conjunction with a drive unit of the system. The following description of the software includes details of the user interface, operational, and safety and security requirements. The software also contains a Help file.

The software is specific to the drive unit electronics and will not operate with other versions of the hardware. The device hardware which may be referred to throughout this text includes the following: Mechanical Auxiliary Ventricle Rev. 3.0 (MAV) and Components: Wearable Drive Unit (WDU); Line Powered Drive Unit (LPDU); External Drive Line; Percutaneous Access Device (PAD); and Blood Pump. The Personal Computer (PC) software is referred to as WinMAV.

The software product provides straightforward access to a Drive Unit, as well as offers data storage and analysis options. All operations are menu driven. Navigation through the menu hierarchy uses standard keyboard and mouse functions for user friendliness. In addition, help screens and status bars are provided to reflect menu functions.

The software is designed to monitor the patient ECG (and other signals) in real time. However, the software is not intended as a patient monitor, due to the specific requirements of the drive unit hardware, as well as the non-standard cardiac leads. In addition, these signals may be stored and reviewed at a later date. As such, data scrolling, storing, and analysis tools are provided as part of the software design.

The software product also monitors device operating parameters at a number of different times. Such parameters can be stored in the drive unit memory, retrieved from the unit while pumping, or stored to disk and reviewed at a later time. In addition, the software will enable operating parameters to be adjusted and a number of direct operating commands to be issued.

The remaining part of this description contains information on the general function of the WinMAV software. It describes basic system configurations as well as detailed requirements. A general description and overview are provided below.

Data Security and Integrity Requirements describes the protocol required for accurate and secure communications between the PC and drive unit. In Menu Structure and Data Storage, detailed requirements of menu hierarchies are presented both in the text and graphically. In addition, directory and file naming schemes as well as menu navigation rules applicable to all menus are discussed. Finally, detailed requirements for all menu functions are presented in DU Control Menu Functions.

The PC can be connected to either a wearable or line-powered drive unit, which is part of the overall Mechanical Auxiliary Ventricle (MAV) system. A brief overview of the device is presented in this section to provide perspective on the computer interface and device control.

The purpose of the MAV system is to provide diastolic augmentation to patients who display low cardiac function or cardiac deficiency. It is targeted to be a permanent, implanted cardiac assist device driven by an external system including an embedded computer, a compressor, a reservoir, solenoid valves, pressure sensors and signal conditioning circuits. The line powered drive unit incorporates a second reservoir and isolation chamber. The software for the drive unit is flexible enough to manage patient to patient variations in ECG and blood pressure profiles, which are taken into account during the calibration modes of the unit. The ECG is monitored continuously and is used as a trigger whereas the patient blood pressure is monitored periodically. After these pressure measurements, which are made on both a fixed interval and upon the detection of changing patient conditions, timing parameters of the pump are updated.

The unit functions independently from other instrumentation, and the line powered unit automatically switches to DC operation upon line power failure or disconnection. The software performs a self test immediately upon power-up and begins the pumping sequence after performing a purge/fill cycle (in the case of the line-powered unit) and an aortic pressure measurement.

All modes of operation are designed to keep the transmembrane pressure below 80 mm Hg. Should the pressure rise above the safety margin for the blood pump or if data is not within specified limits, the system enters a safe power down mode. Watchdog timer provisions are also made in both hardware and software to recover from any system error which may cause the CPU to enter an undefined state. In addition to shut down and alarm states, error conditions are recorded in the device's non-volatile memory.

The PC communications software (WinMAV) provides the authorized user access to the drive unit for both interrogation and control of device function. During factory development and final preparatory initialization of the device, WinMAV provides a means to ensure electrode and sensor integrity as well as evaluate overall device function.

After the patient is equipped with the unit, the WinMAV software provides the clinical staff a means to periodically monitor the patient's condition as well as the device history. In addition, it is the WinMAV software which will allow the staff to adjust device operating parameters, which are patient dependent, and then monitor the effects of changing these parameters. The recording and file saving features of the software also provide a means of tracking the history of both the patient's condition and the device operation over an extended period of time.

Given the critical nature of the patient parameter adjustment, serial communication of WinMAV will follow standard extended RS-232 protocol with the addition of several layers of protection to guard against unauthorized access to the device. While data integrity is protected with the stringent communications checking schemes, security is ensured by both a physical connection to the device which is a non-standard proprietary connector and communications command sequences which are encoded. In addition, all users qualified to alter the patient table are issued a Password for authorization on the PC. Finally, the software protects against erroneous parameters by rejecting any attempt by the user to enter values which fall outside pre-determined safety limits.

The software restricts user access. Communications protocols are sufficient to ensure data integrity and security. Drive unit identification is checked prior to any access. In addition, the software will ensure that all modified patient parameters fall within pre-defined acceptable ranges of safety.

Three levels of user access are defined in Data Security and Integrity Requirements. Level 1 allows viewing of recorded data files only. Level 2 access allows modification of operating parameters necessary to treat the patient on a daily basis. The third level of access is more stringent and shall be referred to Level 3 access. This level is required to minimize inadvertent changes to settings that should be factory adjustable only.

The authorized user is able to view patient signals from the drive unit. These signals may be recorded and stored to disk during the real time display, and the user can freeze the display and perform measurements on any of the displayed waveforms.

The drive unit software continuously updates a snapshot buffer of the machine state and several physiologic parameters. A number of error conditions result in drive unit storage of this snapshot at different times during operation. The software allows the authorized user to download, view, and store these records to disk as well as view current operating conditions.

The parameters in the patient table in the drive unit memory are used to set operating parameters as well as determine physiologic conditions such as an arrhythmia or deviation from normal sinus rhythm. The software allows the authorized operator to access, retrieve, and update the patient parameter table while ensuring that safe limits of these parameters are maintained.

The physician or other authorized operator can execute drive unit operating commands directly from the PC. The software also allows memory resets during factory updates or normal operating mode. A full drive unit reset to factory defaults requires Level 3 access.

The software allows the operator to review previously recorded data streams. Much of the off line processing functions are similar to those under real time control. These include freeze frame and measurement screen display modes.

Also, there are functions for storing data to disk in a format compatible with current database programs.

The software requires, as a minimum, a 120 MHZ Pentium PC with 16 MBytes RAM. Hard disk space requirements are based on the number and length of real-time records to be saved. In addition, the operating system shall be Windows 95, Windows 98, or Windows NT.

The extended RS-232 protocol ensures integrity of data transfer. The other layers of security described in Data Security and Integrity Requirements protect against unauthorized device access. Hard coded safety limits to device parameters ensure a safe operating environment for the patient in terms of device settings. The drive units provide multiple layers of hardware and software safety design techniques for added protection.

An operator can access data and issue selective commands to the drive unit at any time during operation. The link is made from a local PC running the WinMAV software. Alternatively, the connection can be made via modem which requires that the physician instruct the patient on the connection procedure over a separate phone line. In either case, serial communication follows standard RS-232 protocol with the addition of several layers of security protection including user name and password authorization on the PC.

There are three levels of security access to the system. Each succeeding level requires additional information from the user, and is therefore more difficult to access. The levels are described in detail as follows:

Level 1: No security protocol is required for access. The user name and password are not required. The only function available is the viewing of stored data files on disk.

Level 2: The required access codes include all three data items, which include the user name, password, and machine ID. This level of access allows the physician or technician access to all normal modes of operation. This includes all previously mentioned functions as well as real time display, command functions, parameter table modifications, and history record and snapshot information. This level also enables the user to reset the event log, which automatically makes a copy of the record to disk. Finally, the user may set the drive unit to a pacemaker trigger mode, which ignores the normal QRS signal. The latter command must only be done under physician approval and under given specific circumstances.

Level 3: This level of access is meant for factory authorized personnel only, and is accessed by use of a specific machine ID. The functions that may be accessed include stroke volume calibration, and execution of the Reset DU (reset the drive unit) command.

An additional mode that is outside the normal access levels allows updates of authorized users. A separate password allows an authorized user to modify the list of personnel allowed to access the drive unit and modify their passwords.

Figure 7:
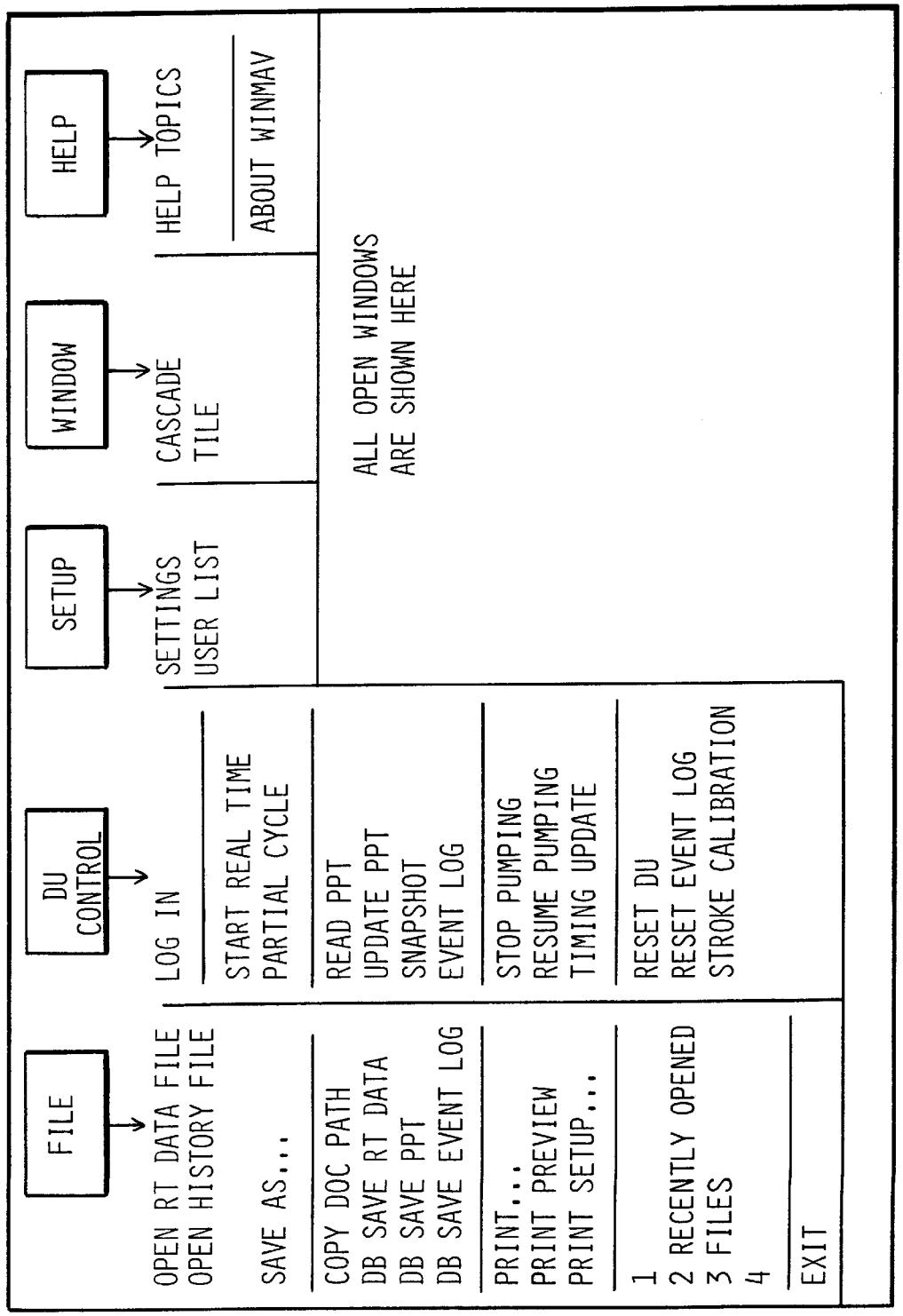
FIG. 7 is a main menu structure of the Win MAV Communications software.

All command functions are menu and/or tool bar driven for user ease. The structure of the menu hierarchy is presented in FIG. 7. The menu selections appear at the top of each screen, similar to other Windows programs. Directly below the main menu, the tool bar is available to automate more frequently used tasks. The user can scan menu selections using designated keys or a mouse. Unless the PC is occupied with real time data update and display, a help button is provided to describe menu command functions. In this section, top-down menu structure overview and navigation rule specifications are furnished.

The top level menu functions are accessible via the keyboard or the mouse via a pull down menu structure. Left and right arrow keys, the <enter> and <escape> keys, <alt>+keyboard keys (underlined letters on the menu), mouse movement and both mouse buttons control program execution.

Alternatively, pressing the left mouse button while positioned on any tool bar button results in command execution. Positioning the cursor over any tool bar button (without left clicking) opens a small text window which describes the button. Also, a more verbose description is given at the bottom left portion of the screen.

Specific menu functions are presented in DU Control Menu Functions. Keyboard and mouse actions result in accessing the functions shown. The highest level menu items separate the WinMAV functions into the following five categories:
(1) File: Device error statistics and real time data files can be viewed, stored to disk, and printed from this menu. Additionally, several functions for database compatibility are incorporated.
(2) DU Control: All drive unit command and control functions are accessed from this menu. First, the log in screen establishes user access and restrictions as well as confirms the correct drive unit identification. Drive unit control functions include real time display, parameter table manipulation, system commands, and non-volatile memory control.
(3) Setup: Includes real time display channel selection and sweep speed, communication port selection, as well as the user list update functions.
(4) Window: Standard Windows function which allows various open window arrangement tools. Also, if windows overlap, the foreground window can be selected from a list of open windows.
(5) Help: Standard Windows function that allows the user to search for a function or command from an indexed list. Also, the program name, version number, and copyright notice are found under the "About WinMAV" selection.

The tool bar is a shortcut means of accessing various communication and control functions.

These functions are summarized (from left to right) as follows:
(1) Open a real time data file for viewing. The graphical representation is similar to the actual file, showing an ECG and drive line pressure waveform.
(2) Open an event log, or history record file. Depicted by a dinosaur.
(3) Print current data window. Icon depicts a printer.
(4) Previous screen. Stored file navigation tool, depicted by an arrow to the left.
(5) Next screen. Stored file navigation tool, depicted by an arrow to the right.
(6) More data (zoom out). Depicted by a binoculars.
(7) More details (zoom in). Depicted by a magnifying glass.
(8) Make measurement. Depicted by a calipers.
(9) Initiate a partial cycle. Shows a partial cycle as seen in the real time display waveform, and abbreviated by the letters PC.
(10) Begin real time data display. Shows a real time ECG waveform and the abbreviation RT.
(11) Stop, or freeze real time display. Depicted by a snowflake.
(12) Begin recording data to disk. Depicted by a floppy disk icon.
(13) Stop recording data to disk. Depicted by a floppy disk icon with a line through the middle.

Several of the above buttons may be unavailable due to the current mode of the system. The unavailable functions are indicated graphically by muting the color of the button. In other words, the button is "greyed out". For example, prior to logging in to the system, only the open file functions are available.

In addition to the menu at the top of the screen, status information appears at the top and bottom of each window. This is intended to provide brief help information, or show additional data about a particular file. The default message displayed at the bottom of the screen is For Help, Press F1.

The status information is displayed based on the cursor position. When the cursor is positioned over a particular tool bar button, a small description of the button appears, if the mouse remains in that position. The information is in the form of a small window at the location of the cursor. Also, the status bar displays the same information.

There are two types of files which may be saved during normal operation of WinMAV. These are: (1) real time data acquired by the drive unit and the set of patient specific parameters, which sets a number of device functions, and (2) the record of device history and error statistics. Regardless of specific file content, common rules govern file naming and directory location, as outlined below.

The drive unit serial number is extracted from the Machine Identification Code and used as a directory name for all files associated with that particular unit. The directory itself is created by WinMAV at Log in time, but only if the user has Level 3 access (highest level). If no such directory is detected at run time, the application reports an error. Data file names are generated automatically by the software, and each name is unique and reflective of the data type. The name includes a time stamp, named for example in the format "yy_mm_dd_hh_mm_ss.drt" where "yy" is the year, "mm" is month, "dd" is day, "hh" is hour (24 hour format), "mm" is minutes, and "ss" is seconds. The file extension is "drt", which indicates this is a real time data file. The Patient Parameter Table is automatically stored with the real time data, and is always part of the real time display window.

History record files use the same file format, but with an "hst" file extension.

If the user wishes to add a new drive unit to the list without having Level 3 access, a directory may be created using standard Windows tools. For example, the Windows Explorer can create a new folder in the WinMAV root directory (examples as follows);

L15 Line powered drive unit, serial number 15
W2 Wearable drive unit, serial number 2.

An error message is generated if there is a directory search failure. Each generated file is stored in the appropriate directory and bears a unique name, reflecting its data type.

The off line processing menu selections allow the operator to review previously recorded data. As noted in Log In, the user need not log in to access stored files. Functions that are available are any of the File open commands (event logs or real time data files), the Log In command from the DU Control menu, and the Settings function from the Setup menu.

Much of the off line processing functions are similar to those under the Start Real Time menu. The functions launched during off line processing differ from those which are sub-functions of the Start Real Time menu in the following ways:

(1) There is no channel selection on the stored file. If only two channels were selected for recording, the third channel will not be available in the record.
(2) A seconds counter is displayed across the bottom of the first channel to allow the user to navigate very long records, or note when events occurred in a record.
(3) The addition of Previous Screen and Next Screen tool bar buttons allow the operator to scan the record one frame at a time.
(4) The background is black (during real time measuring, the background is blue).

Upon execution of an open command from the File menu or selection of a shortcut button from the tool bar, a window will pop-up that allows the user to select a file with a default extension that matches the format to be accessed. The standard Windows navigation tools are available to find the desired file.

Once a file is opened, the real time display window shows the waveforms that were selected by the Setup function. The patient parameter table is visible on the right side of the real time window, and can be resized to show more or less of the real time data. The background color of the data window is black, to distinguish it from real-time data if multiple windows are open. Real-time data windows use a dark blue background color.

The tool bar buttons for data measurements are active as well as the More Data and More Details functions. These features allow measurements of time and amplitude on any stored real time waveform. Older files that were created by the DOS version of the program can be loaded into Win-MAV and then saved in the new format. Comments may be added at any time after the files have been stored. The File:Save As menu function adds the comments to the file.

In order to save the files for later storage, analysis, and retrieval from a database program, two File menu functions are implemented. The first is DB Save RT Data, which saves the real time data file in a format that can be recognized by the database. The second function is DB Save PPT, which performs the same function but strips the Patient Parameter Table from the real time data.

Another database tool is the Copy Doc Path function from the File menu. This tool copies the DOS path and current temporal position of the data file to the clipboard, which can be retrieved by the database for simplified file pointers. For long real time data files, this allows access to a particular point in time within any data record to be viewed by the database program.

The Log in Window requires three pieces of information. The Operator Initials are used to keep a record of user modifications to the parameter table, as well as who recorded data to a particular file. Initials can be one to three characters in length, and are automatically converted to capital letters. The second item is the unique user Password, which consists of five to ten characters. The third item is a code which consists of the following information. Each drive unit has a unique Machine Identification Code hard coded into its memory, which corresponds to the drive unit serial number. All users are provided with the scheme of the code naming which is a single continuous word containing the general fields shown below:

<type> L for line powered, W for wearable
<id> Machine serial number
<secret> Code known only to users

EXAMPLES

L5<secret>—Line powered drive unit #5
W12<secret>—Wearable drive unit #12

No special access codes are required to view recorded data files. This is defined as Level 1 access.

The second layer of security (Level 2 access) requires all three pieces of information as described above. To this end, each user is given a user name (Physician Initials) and Password. The password is case insensitive.

As described previously, for Level 3 access, a special Machine Identification Code allows access to functions designated for factory authorized users only. This is designed to protect the patient and the drive unit from incorrect settings and avoid the loss of data.

Once the Log In command is issued from the DU Control menu, the user is prompted with a pop-up log in screen. The <tab> key is used to cycle through the fields. Input from the keyboard is echoed in the fields, except that each Password entry and Machine ID appears as "*" for security. A carriage return, or selection of the OK button completes the log in operation, and the pop-up screen will close. Information is verified and either allow or deny access appropriately.

In the event the user inputs invalid information, the program reports the following error: "Incorrect log in data. Access denied!". The user will then be restricted to Level 1 access until correct data is input.

Similarly, if the Operator Initials and Password are input correctly but the drive unit ID number is incorrect, a message will pop-up indicating the error as follows: "Incorrect drive unit ID. Please log in again." This error will not be generated until the user attempts to communicate with the drive unit.

Drive unit control menu contains all drive unit real time display and control functions. One of these functions is the Start Real Time mode. The authorized user can view up to three channels of data from the drive unit. The possible channels are: (1) ECG, (2) MAV Drive Line Pressure, and (3) Differential Pressure. One purpose of the Real Time menus is to allow viewing of any combination of these signals at any time during drive unit operation. Gain, display sweep speed, and offset adjustments to the waveforms shown on the screen are available. In addition, signals may be recorded and stored to disk during the real time display of the data.

The user can also freeze the display and perform timing and amplitude measurements on the desired waveform. Finally, the Read PPT menu options are available from the first level of the DU Control menu. This allows the operator to adjust patient parameters and see the effects of these changes without leaving the Real Time menu tree. However, the parameter table adjustments are available only when the display is frozen.

Figure 8:
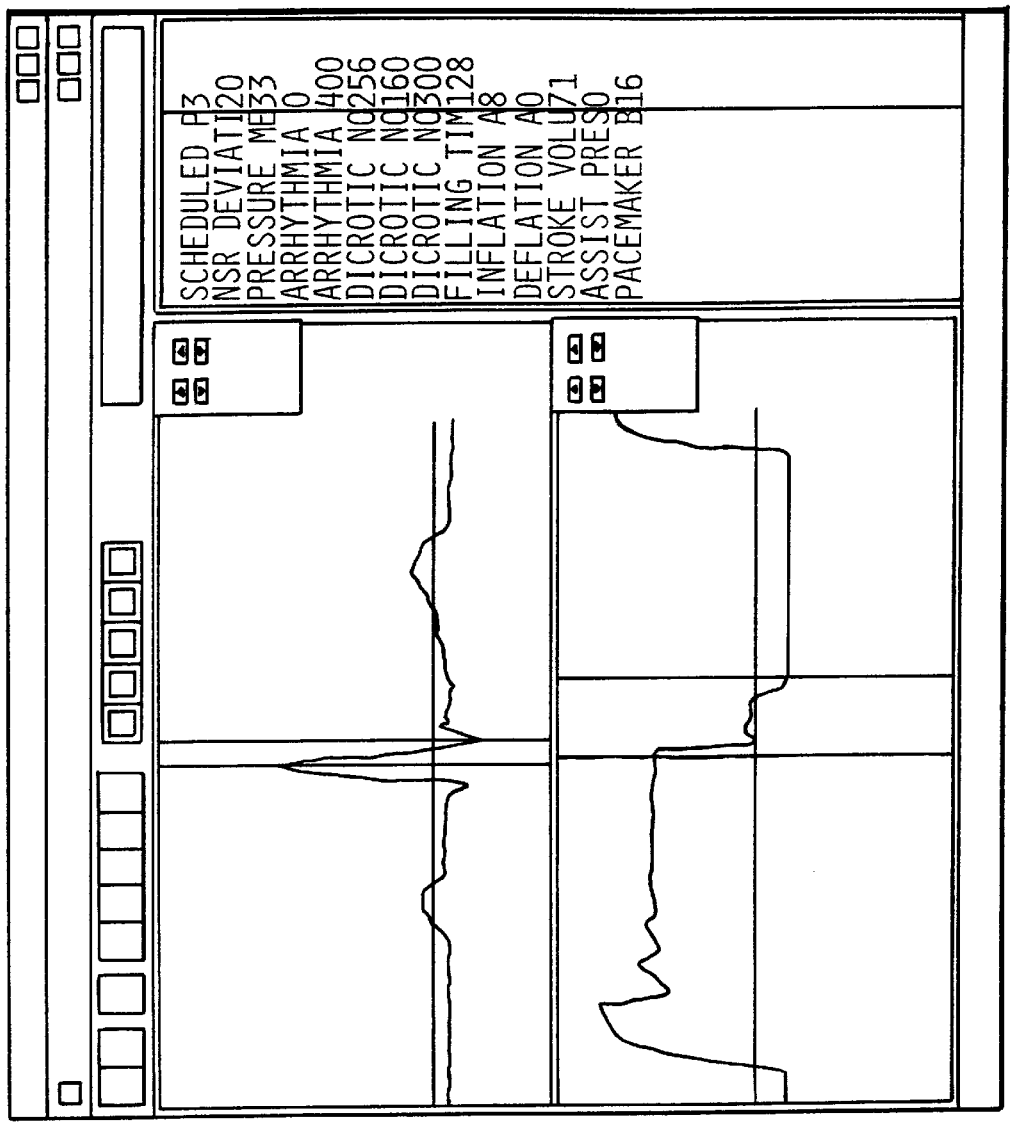
FIG. 8 is a screen shot of a sample measurement window and cursors.

Once the data acquisition setup has been entered and the user has correctly logged in with Level 2 access, real time display can be initiated. As stated in Start Real Time and shown in FIG. 8, there are two windows visible. One is the actual display of the selected channels, and the other is the Patient Parameter Table.

In addition to the real time data stream, the drive unit sends its operating, or machine state. The various machine states appear as different colors on the displayed waveforms. A color scheme similar to the one below is used:

| Signal | State | Color |
| --- | --- | --- |
| ECG | R-wave detected/absolute blanking | light blue |
| ECG | T-wave (partial) blanking | gray |
| ECG | Pacer spike | red |
| ECG | Other (searching for R-wave) | green |
| MAV/Diff | Filling time | magenta |
| MAV/Diff | Deflation | light blue |
| MAV/Diff | Other | gray |
| BACKGROUND | N.A. | dark blue |

The buttons available during real time display are as follows: More Data; More Details; Stop/Freeze; and Start Recording. Buttons on the tool bar that are available after the screen is frozen: Open RT File; Open Event Log File; Print; Previous Screen; Next Screen; More Details; More Data; Measurements; Partial Cycle; and Start Real Time.

The Baseline is always visible in the real time window, regardless of whether the display is frozen or not. It consists of a horizontal line drawn across the screen and corresponds to the baseline signal value, which is defined as (1) the average value of the signal in the case of the ECG, (2) atmospheric pressure in the case of the MAV drive line pressure, and (3) zero difference in the case of the differential pressure sensor signal.

Activation of the Measurements button, in addition to the appearance of the cursors, causes a small text box to appear within the data viewing window.

Three values of interest appear in the text box:
(a) abbreviation for "absolute", represents the value of the signal where it intersects the last moved cursor and the baseline value.
(d) the "difference" in amplitude values of the signals at the cursor intersection points.
(t) the amount of "time" elapsed between the vertical cursors.

The up and down arrows at the top of the box allow adjustment of the position and size of the waveform. Specifically, the left set of arrows adjusts the offset, while the right set of arrows adjusts the gain. Each click of the mouse on the arrow will incrementally increase or decrease the offset or gain.

The Start Recording button will begin saving the raw data to the real time data file given the naming protocol described in File Naming. During recording of the signal(s), the screen continues to scroll and display the signals as they were in the Real Time:View screen. It should be noted, however, that the data will be saved just as it was sent from the drive unit, without any gain or offset adjustment. During the recording process, the only buttons available are Stop Recording and Stop/Freeze.

The Stop Recording command automatically labels the record with default comments that include the Operator Initials and Drive Unit ID, for sorting during playback. Also, the comments that are present in the comments portion of the tool bar are saved to disk.

Also included in the file of real time data is the patient parameter table. The purpose of recording this information, is to allow retrieval and display of pumping parameters along side the real time data.

Each real time record that is saved to disk has a header that is unique to a type of drive unit (either WDU or LPDU).

The purpose of partial cycle function is to allow the user to determine if the machine settings are correct for detection of the dicrotic notch. There are two methods for performing a partial cycle. The user can either choose Partial Cycle from the DU Control menu, or select the PC button from the tool bar. In either case, the machine enters a state where the real time display will continue for the current display sweep only. Then the display will freeze and perform a number of calculations.

One of the most important concepts for setting up the drive unit timing is the concept of the "window" for detecting the dicrotic notch. The simplest explanation is that the window is the most likely time that the dicrotic notch is to occur after the detected R-wave. It should be wide enough to encompass any expected heart rate for the patient in question, barring any problems such as artifacts which may cause false detections.

After the screen is frozen and the detected notch is shown on the display, it is then up to the user to determine if the drive unit has correctly detected the dicrotic notch. If it is correct and the window for detection is reasonable, no action is required, except perhaps to save the record for future analysis. If the drive unit has incorrectly found the notch, the user must take further actions to ensure correct drive unit operation.

A reasonable window for detection must be defined on a patient to patient basis with the authorization of a physician. Even if the window is appropriate given the current patient status, if conditions change dramatically the settings may be inappropriate.

When the user activates the calculations function, a command is sent to the drive unit to perform a timing update. After the partial cycle is complete and the display is frozen, the PC performs the following functions:
(1) Calculate the mean, systolic, and diastolic patient pressures and display the result at the bottom of the screen.
(2) Show where the computer found the dicrotic notch using the cursors, and display the time from the ECG to the notch in milliseconds.
(3) Show the method the computer used to find the notch (either fastest slope, actual notch, or nothing found—default).
(4) Display a colored bar at the top of the drive line pressure waveform which indicates the current "window" for detection of the dicrotic notch. This window consists of the dicrotic notch earliest, latest and default settings.
(5) Finally, the user may obtain a suggested set of settings for the dicrotic notch detection window.

In an example of the partial cycle measurement, if there is no ejection, the status bar at the bottom of the screen indicates this with the (Default) text. The first cursor shows the point of detection of the R-wave. The second cursor shows where the dicrotic notch was found, or if not found, the default setting. At the top of the second trace overlapping the second cursor, is a small horizontal bar. This bar indicates the "window" for dicrotic notch detection, which includes the parameter table settings as described above.

To continue real time display, the user must either select the RT button from the tool bar, or select Start Real Time from the DU Control menu.

The user should not select the freeze button during the partial cycle sweep. This action will stop the calculations and halt the real time trace.

The authorized operator can access, retrieve, and update the patient parameter table. The parameters in the table are used by the drive unit to determine conditions such as an arrhythmia or deviation from normal sinus rhythm as well as to set operating parameters such as filling time of the blood pump. The actual adjustments are made via WinMAV by an operator authorized as described in Log In.

When the Read PPT button is executed from the Du Control menu, the software will issue a command to the drive unit to send the table. After receiving the patient parameter table, the module will save the table values locally and display them.

Modification of parameters is done by double-clicking on the desired parameter, and adjusting the slider control or entering values directly. The default value is shown in square brackets, and always visible in the left corner of the slider bar window. Clicking on the OK button completes the adjustment of the local parameter table. Note that the drive unit has not yet received the updated values.

The second method of changing parameter table values is from within the real time display window, but only when the sweep is frozen. The method is the same as discussed above.

After all desired parameters have been updated, the Update PPT selection from the DU Control menu sends the data to the drive unit. The drive unit will receive the data and perform a CRC. If every check scheme verifies data integrity, the patient parameter table is be updated.

A simplified means of changing the dicrotic notch window settings (dicrotic notch earliest, latest, and default) is available. The method suggests a window for detection that is ±30% from the detected dicrotic notch. The default setting is equal to the detected dicrotic notch plus 50 ms. The feature is activated by clicking the right mouse button in the real time window after the Partial Cycle command has been executed. A confirmation window will pop-up asking if the user wishes to accept these settings. Selecting Yes will write the suggested values into the parameter table, but will not update the drive unit. The user should verify that the notch has been detected properly before accepting the values. After the drive unit operating parameters have been updated, the next Scheduled Pressure Measurement uses the new window when searching for the dicrotic notch. The final action is to send the parameter table with the updated values by selecting the Update PPT function from the DU Control menu.

As an additional safety feature, the allowable limits for each edited parameter are displayed. Any value entered which exceeds or falls below the specified limits will be ignored. It will thereby be impossible for any operator to modify a parameter to a value outside of the pre-determined safety zone.

If the user attempts to close the parameter table window after changing values and has not sent the values to the drive unit, a window shall pop-up as a reminder to send the data to the drive unit. The user has the option to ignore the changes, or send the table.

In order to obtain an on-line description of each parameter table setting, the user can consult the help menu. The help windows reflect the brief descriptions below.

(1) Scheduled Pressure Measurement. This refers to the amount of time between partial cycles for MAV drive line analysis.

(2) NSR Deviation. This parameter sets the % deviation allowed between the last average R—R interval and that measured during the most recent partial cycle, considered normal sinus rhythm (NSR).

(3) Pressure Measurement Lockout. A timing update can be the result of NSR deviation. Frequent detection of this deviation would result in frequent partial cycle measurements. For patient safety, an absolute minimum time between partial cycle measurements is set with this parameter.

(4) Arrhythmia Threshold. An arrhythmia is diagnosed if the arrhythmia index described exceeds this threshold.

(5) Arrhythmia Inflate Delay. This parameter refers to the conservative setting of the inflate command, which is set upon the detection of an arrhythmia.

(6) Dicrotic Notch Default. This parameter refers to the value used as the dicrotic notch time if one is not found within the prescribed time interval.

(7) Dicrotic Notch Earliest. This parameter sets the time limit for the earliest detection of the dicrotic notch. Note that the table values show an overlap of the earliest and latest settings for notch detection. The software will not allow the user to set these values incorrectly (i.e.: enter a value of 450 for Dicrotic Notch Earliest and 300 for Dicrotic Notch Latest).

(8) Dicrotic Notch Latest. This parameter sets the time limit for the latest detection of the dicrotic notch.

(9) Filling Time. This is the target value for the inflation duration.

(10) Inflation Adjustment. The "inflate valve open" command is set to precede the dicrotic notch ($t_{DN}$) by a maximum of N msec to allow for mechanical delays in the system. The Inflation Adjustment (IA) parameter defines a delay such that inflation begins at a time equal to (IA−N) msec relative to $t_{DN}$. The shortcut mode of adjustment is to use the Real Time plus and minus buttons in the adjustment window for modification of Inflation Adjustment and Deflation Adjustment parameters. The appropriate parameter is changed in the parameter table and the table is immediately sent, thereby updating the drive unit values. The user is not required to select the Update PPT button.

(11) Deflation Adjustment. The time between the R-wave trigger and the deflation command is set by this parameter. The shortcut mode is the same as in (10) above.

(12) Stroke Volume. This parameter sets the desired percent inflation of the blood pump. The calibration of the volume control algorithm is set at the factory.

(13) Assist Pressure Correction Factor. This is the value used to estimate aortic pressure at the end of inflation from values measured during a partial cycle.

(14) Pacemaker Blanking. The hardware detects the pacemaker pulse and signals the processor via an interrupt line. R-wave blanking begins when this pulse is detected and extends for the period selected in the parameter table. While this blanking is in effect, the real time display color is changed from green to red.

If the above parameter is set to zero, a mode is entered that forces the R-wave detector to trigger only on the pacemaker pulse. This pulse is detected in hardware and may not be visible on the display, but the signal should turn from green to red as discussed previously.

When in pacemaker trigger mode, the parameter table will display a zero with a series of exclamation points (0!!!!!) As a visual reminder that this mode is in effect.

TABLE 2

Range of Acceptable Patient Parameter Values

| Parameter | Units | Minimum | Default | Maximum |
|---|---|---|---|---|
| Scheduled Pressure Measurement | min | 3 | 10 | 20 |
| NSR Deviation | % | 10 | 20 | 80 |
| Pressure Measurement Lock-Out | sec | 15 | 30 | 60 |
| Arrhythmia Threshold | % | 0 | 10 | 15 |
| Arrhythmia Inflate Delay | msec[1] | 250 | 400 | 500 |
| Dicrotic Notch Default | msec | DNE entry | 300 | DNL entry |
| Dicrotic Notch Earliest (DNE) | msec | 150 | 180 | 450 |
| Dicrotic Notch Latest (DNL) | msec | 300 | 350 | 552 |
| Filling Time | msec | 60 | 96/128[2] | 160 |
| Inflation Adjustment | msec | −80 | 28 | 50 |
| Deflation Adjustment | msec | 0 | 0 | 152 |
| Stroke Volume | % | 25 | 100 | 110 |
| Assist Pressure Correction Factor | mm Hg | −20 | 0 | 50 |
| Pacemaker Blanking | msec | 12 | 20 | 80 |
| Pacemaker Trigger mode | | 0 | N/A | N/A |

[1]The millisecond values in the table are stated as round numbers, however the program only has 4 millisecond resolution. Therefore, the listed value is only an approximation. The actual value will be rounded to the nearest multiple of 4 milliseconds.
[2]The WDU default filling time is 96 ms, while the LPDU default setting is 128 ms. These values have been chosen to maximize augmentation while minimizing oscillations in the compressor speed control servo.

The drive unit software continuously updates a snapshot of the current machine state. Memory is allocated for a minimum of 20 possible "detected event" snapshots and a minimum of 21 or 28 event counters for the wearable and line-powered units, respectively. Due to memory limitations, the state of the machine is stored only at the time of the initial occurrence of an event. Detailed records of subsequent events are not stored; however, the number of times each event occurs is recorded.

Thus, at any given time, the drive unit memory contains (1) the current operating snapshot, (2) the collection of snapshots, and (3) event counters for each error condition. Items (2) and (3) constitute the history record or Event Log of the device.

When Event Log is selected from the DU Control menu, a window appears that shows all recorded events for that particular drive unit. The window displayed contains three sub-sections. The first, leftmost section includes the numbers of the available snapshots. The OP labeled snapshot is for the operating snapshot (may or may not be generated by an error). The second section includes the snapshot data for the selected snapshot from section one. Finally, the third section contains the statistical data for each error. The user simply selects the snapshot to be viewed, and the appropriate data is displayed. The line labeled Error Code that is present in the snapshot section is highlighted along with the error statistic in the third section.

When an error is detected and the Event Log is downloaded, the first snapshot is highlighted by default. However, this is not the current error that was just detected. In order to determine the most recent error, the user must select the operating snapshot to see the event data. A means of verifying that this is the correct error is to check the date and time stamp of the error.

In order to save the Event Log data to disk, choose the Save As command from the File menu. This command generates an automatically and uniquely named file which stores the entire history record and the operating snapshot.

The information stored in the event log is as follows:
(1) Event Code. Each type of flagged event will have a corresponding event code.
(2) Time Stamp. Time elapsed since last power-up will be recorded.
(3) Working Time. The amount time mechanical parts have been in operation since the unit left the factory will be recorded.
(4) Dicrotic Notch Time. The time of the "found" dicrotic notch will be recorded along with an indicator of which criterion was met (slope change versus maximum slope).
(5) R-wave Detection Thresholds. These entries include both the current slope and amplitude thresholds.
(6) Arrhythmia Quotient. This parameter is the current value of the arrhythmia detection quotient.
(7) NSR deviation. This value refers to the current difference between the last average R—R interval and that measured during the most recent partial cycle.
(8) Filling Time. The most current value of the inflation duration (ID) variable and target ID will be recorded.
(9) Motor Speed Parameter. The current % modulation or duty cycle will be recorded.
(10) Integration Sums. These values refer to the current value and target value of the accumulated ΔP summation used for volume determination.
(11) Pressure Gradient. This is the current estimate of the difference between the MAV drive line pressure and the aortic pressure at the end of inflation.
(12) Reservoir Pressures. The maximum and minimum pressure of each reservoir (during the last cycle) will be recorded (the Wearable Drive Unit has only 1 reservoir).
(13) Partial Cycle Time. This refers to the amount of time expired since the last partial cycle and MAV drive line waveform analysis.
(14) Patient Conditions. The patient parameters determined from the most recent drive line analysis will be recorded. These include: (i) mean aortic blood pressure, (ii) systolic peak pressure, (iii) blood pressure at the dicrotic notch, (iv) the minimum aortic pressure, and (v) the average R—R interval.

The only states that are displayed in the event of an error are the actual error condition or machine state. In the case where an error has not occurred or the state has not been defined or initialized yet, the state or error shall read N/A. Other parameters shall denote a lack of information via the words "Unknown", "No Data", or with zeroes in the case of undefined numerical readings.

Self test modules are performed prior to pumping, and an error condition is produced if any test condition is not satisfied. In addition to these specific device function tests, a number of operating conditions will be evaluated throughout normal operation. In the event of any error (self test or operational), an alarm will sound (beep), an LED will be lit, and an action will be taken. There are 3 LED indicators on the unit which correspond to different types of errors: (1) Battery Status (yellow), (2) Connection Error (red), and (3) System Error (red).

In addition, the battery status LED will flash (0.5 Hz) in the event of a low battery condition. The detection of most errors will effect a power down sequence, which turns the motor off and enters a default valve state, which results in deflation of the blood pump. All detected errors will be recorded in the error log. The following items describe some of the more common error conditions and system responses which may occur during normal operation.
(1) Line Power Disconnected: If the line power is disconnected from the drive unit, the hardware automatically switches to battery operation and signals the processor. The patient/operator will be alerted any time the power supply switches over to battery operation. The Caution alarm will sound twice (10.5 seconds total) and the Battery Status LED will flash for 10 seconds.

(2) Battery Capacity/Status (Error 02): The battery status is monitored throughout normal operation. The voltage is monitored once every acquisition cycle (every 4 ms). A level below a pre-determined value constitutes a "low battery" condition. A level below a second (lower) pre-determined value constitutes a "discharged battery" condition. The low battery condition will cause the Battery Status LED to flash and the Caution alarm to sound. Under the discharged battery condition, the Battery Status LED will be activated continuously, the Warning alarm will sound, and the unit will be powered down.

(3) Detached Drive Line (Error 03): A disconnected drive line will prohibit operation of the pump. The error condition will result in the activation of the Connection Error LED, the Warning alarm will sound, and the unit will be placed in the power down state.

(4) Temperature Shut Down (Error 04): Component operation causes some heating within the unit housing during normal pumping. Excessive heat or cold may cause unreliable operation. If a temperature outside of the operating range is detected, the System Error LED will be activated, the Warning alarm will sound, and the unit will be powered down.

(5) Pressure Reservoir Pressure Out of Range (Error 14 (low) and 15 (high)): During normal operation, the pressure reservoir tank is being pressurized at all times except inflation. Although the safety relief valve will be checked during the self-test, its operation will be ensured by continuous monitoring. In addition, an "insufficient pressure" condition would indicate possible valve leakage or inadequate compressor function. If the reservoir pressure falls outside of its expected range, an error will result. The System Error LED will be activated, the Warning alarm will sound, and the unit will be powered down.

(6) Vacuum Reservoir Pressure Out of Range (LPDU only, Error 26 (high) 27 (low)): The vacuum reservoir tank is being evacuated at all times except deflation. As with the pressure reservoir, the relief valve will be checked during the self-test and its operation will be ensured by continuous monitoring during normal pumping. An "insufficient vacuum" condition would also indicate possible valve leakage or inadequate compressor function. An error will result if the reservoir pressure falls outside of its expected range. The System Error LED will be activated, the Warning alarm will sound, and the unit will be powered down.

(7) R-wave Lost (Error 16): Correct detection of the ECG R-wave is critical for the proper triggering and pumping sequence. A loss of R-wave detection is likely to be a connection error. If such a loss occurs, the Connection Error LED will be activated, the Caution alarm will sound, and the unit will be powered down.

(8) High Pressure in MAV Drive Line (Error 17): Pressure in the MAV drive line which exceeds a certain limit is a more serious condition than an insufficient pressure scenario. The Connection Error LED will be activated, the Warning alarm will sound, and the unit will be powered down.

(9) High Pressure Gradient Across Blood Pump Membrane (Error 18): Repeated exposure to large pressure gradients across the blood pump membrane could result in premature fatigue. Since MAV assisted aortic pressure cannot be monitored during pumping, this pressure gradient cannot be measured directly during normal operation; however, it can be estimated as follows: The estimation scheme relies on the assumption that relative difference between MAV assisted aortic pressure and aortic pressure during systole remains constant. Prior to the patient's transfer from ICU, arterial pressure is clinically monitored such that systolic pressure ($P_{systole}$) and MAV assisted aortic pressure ($P_{assissed}$) are determined simultaneously. By defining an offset or correction factor (CF) as the difference between these ($P_{assisted} - P_{systole}$), the MAV assisted aortic pressure can be subsequently estimated if systolic pressure is known. (Note: If the systolic pressure and the MAV assisted pressure are equal, the correction factor is zero.) During normal operation of the drive unit, the systolic pressure measured during a partial cycle and CF (stored in the patient parameter table) can be used to estimate MAV assisted aortic pressure ($P_{assisted} = P_{systole} + CF$) Further, the differential pressure across the MAV membrane can be estimated during normal operation as the difference between this value and the MAV drive line pressure ($P_{MAV}$). If the differential pressure exceeds a prescribed level, the System Error LED will be activated, the Warning alarm will sound, and the unit will be powered down.

(10) Blood Pump Pressure Rise While Inflated (Error 18): Pressure rise in the blood pump after the common valve is closed could be indicative of a valve leak. The Connection Error LED will be activated, the Warning alarm will sound, and the unit will be powered down.

(11) Incomplete Deflation (Error 20): Incomplete blood pump deflation is a serious potential error and could indicate a Common valve failure. Upon detection of this error, the unit will be powered down. The System Error LED will then be activated, and the Warning alarm will sound.

(12) Watchdog Shut Down (Error 22): Failure of the watchdog service routine to address the watchdog timer under normal operating conditions is an indication that the CPU has been rendered inoperative. Such an undefined failure cannot be tolerated. In this case, the System Error LED will be activated, the Warning alarm will sound, and the unit will be shut down.

(13) Leak Detection (LPDU only, Error 28): The isolation chamber/drive line/blood pump system should maintain a fixed amount of air during normal operation. Incomplete blood pump deflation can be caused by air leaking into the system. Incomplete inflation or excessive vacuum during deflation could result from air leaking out of the system. By comparing beat-to-beat deflation pre-charge pressures to that measured during the most recent Fill cycle, possible leaks can be detected. Upon detection of a leak, the unit will be powered down. The System Error LED will then be activated, and the Warning alarm will sound.

During normal operating mode or factory updates, the operator may wish to perform several functions which directly control the device. This mode allows the physician or other authorized operator to execute operating commands to the drive unit. Examples of control commands are the ability to start and stop pumping, or initiate a partial cycle.

If the operator has appropriately and correctly logged in, device commands are available from the menu. In the DU Control menu, there are several commands that control the drive unit directly, or change the stored statistics.

Reset DU: Activation of this button is restricted to Level 3 access (factory personnel only) via the special user Machine Identification Code. The button is used to reset the drive unit memory. This command reinitializes all buffers and variables as if the device had never been powered-up. That is, the device memory is reset to its factory values. When this command is issued, the WinMAV software automatically saves the event log to disk, following the prescribed file naming convention.

Reset Event Log: In this case, the History Record and event statistics are reset. As noted in Event Log, the memory allocated for the wearable and line-powered units, respectively, contain a minimum of 20 possible "detected event" snapshots and a minimum of 21 or 28 event counters. That is, the memory limitations of the drive units necessitate that the state of the machines be stored only at the time of the 20 initial occurrence of these events and that subsequent events are merely registered as "counts". As with the above command, the WinMAV software automatically saves the event log to disk.

Stop Pumping/Resume Pumping: The operator may wish to evaluate the patient's condition with assistance versus without assistance. These menu buttons serve to directly control the pumping action of the drive unit.

Timing Update: Activation of this command from the DU Control menu, results in the drive line waveform analysis actions and updates described in the user documentation for each drive unit. Briefly summarized, the drive line analysis will result primarily in an update of the dicrotic notch time and therefore, the inflation command time. In addition, this analysis generates an update record of the most recently determined values of peak systolic pressure, diastolic pressure, mean pressure, and time from the R-wave to the dicrotic notch.

It should be noted that this command does not act the same way as the Partial Cycle command. Although the drive unit performs the same action, the WinMAV program does not freeze the display with cursor indicators, or calculate any patient pressures. Therefore, there is no feedback as to where the dicrotic notch was detected.

Snapshot: As noted in Event Log, the software of the drive unit continuously updates a snapshot of the machine state. In contrast to the Event Log command, as issued from the DU Control menu, this operating snapshot opens a window and provides a button for a New Snapshot. In this way, the user can get several snapshots in succession without going through the normal menu structure.

In addition to the normal functions of the patient parameter table, a calibration mode may be entered. As discussed in Data Security and Integrity Requirements, the factory authorized user with Level 3 access may adjust the definition of 100% stroke volume. If the desired volume is 50 cc (for example), the user may input an adjustment value which increases the output to 50 cc for a setting of 100%.

After the stroke volume calibration is complete, when the parameter table is read the user will not see evidence of the calibration. This information is transparent to the user, and cannot be modified without entering the password specific to this mode.

The first action required is to access the patient parameter table either from the Start Real Time function or the Read PPT function. Then the authorized user can calibrate the system by selecting the Stroke Calibration setting from the DU Control menu. This action brings up a slider window that allows input of values as shown below:
Min: 80% Default: 100% Max: 140%

Once the desired setting has been entered, the user must select the OK button to send the information to the drive unit. In this case, the user is not required to send the data to the drive unit with the Update PPT function. After correct transmission, the communication software responds with a message as follows: "Stroke volume correction was successfully completed!"

Values outside this range are not accepted by the WinMAV software and will bring up an error message warning that the setting exceeds the limits.

At the Settings function of the Setup menu, channel selection, sweep speed, and serial communication port settings are input. The buttons allow selection of ECG/MAV/Diff/None to select the signal(s) to be retrieved from the drive unit and displayed in one or more of the subsequent display windows.

Given the menu selections as described above, the user can select the data display properties for real time waveforms. That is, the data sent to a file reflects the same number of channels as the real time display window. Three channels maximum are available for viewing in any order.

The user may also select the sweep speed via a slider bar with adjustment between Detailed and Epoch. The range of speeds is approximately from one to ten seconds (epoch), with discrete settings in between.

Finally, the user must select the port set up for RS-232 serial communication on the personal computer. On most laptop computers, this will be COM1.

If the wrong port is selected, the WinMAV software responds with a No response from drive unit error message.

The security protocols require the use of a password for access to WinMAV functions that allow modifications to drive unit operation. In order to enable various users to access the system, a user list has been devised to describe all authorized personnel allowed to access the drive unit. The list contains all user initials and passwords, and is encrypted for security.

The factory authorized user who wishes to update the list of users for the MAV system may do so with one security code. This code is entered by selecting the User List function from the Setup menu. At this time, a window will pop-up asking for the password. The password is echoed in the widow with the "*" character as it is entered. Successful entry will bring up a window that includes all authorized users and their password.

The actual list is updated as a simple text file, with standard editing functions available. Each line in the list consists of an entry that includes the initials and the password, separated by one or more spaces.

After the list has been updated, the user should click on the OK button to encrypt the file and store it to disk.

ANIMAL TEST EXAMPLE

This example will discuss the method for logging in, evaluating patient timing, setting up the parameter table, and evaluating drive unit performance. The goal is to maximize the drive unit effectiveness, which will in turn provide the maximum patient benefit.

Execute the program by double clicking on the icon on the desktop as with other standard windows applications. The program will start up with most buttons greyed-out. The first action is to select the Log in function from the DU Control menu. Enter the user name, password, and drive unit ID as discussed in Log In. All necessary functions should now be available.

Prior to activation of the drive unit, the user should evaluate the patient to determine the general timing from the R-wave to the dicrotic notch (or $Q-S_2$) in milliseconds. This can be done via a number of techniques, which will not be discussed in this document. If a peripheral blood pressure is used to determine timing, this pressure is delayed in time by an unknown number of milliseconds. This must be considered when using this pressure for setting up the timing. Assuming that the Q-S$_2$ value is known, this number can be used to select the window for dicrotic notch detection.

At this time, the drive unit can be activated by pressing the Pump On/Off switch. If this is the first time the system has been activated on the patient (in the O.R. for example) the user should immediately go to the DU Control menu and select Stop Pumping. This allows the user to verify correct ECG triggering prior to activating the pump. Pumping must always be synchronous to the heart immediately after the pump has been implanted to minimize the stress on the suture lines. Assuming that the trigger is valid, as shown by the color changes in the waveform, the user can now set up the pump timing.

The window for dicrotic notch detection should be set given the patient evaluation completed earlier. Assuming that the heart rate has not changed drastically, go to the Read PPT selection from the DU Control menu. The resulting pop-up window reflects the current settings in the drive unit. Set the dicrotic notch earliest, latest and default settings as described in Patient Parameter Table. The default value should be about 50 ms later than the current dicrotic notch. Select Update PPT from DU Control when complete. This sends the updated values to the drive unit. If the heart rate has changed since the previous evaluation, the patient evaluation procedure should be repeated. This will ensure that the pump will start with the best possible settings for the current heart rate. The other parameter table values should be evaluated for correctness for the given patient.

Now that the ECG is valid and the pump timing has been adjusted, go to the Resume Pumping selection of the DU Control menu. The drive unit should begin the pump sequence, perform a partial cycle, and pump according to the detected dicrotic notch. The user can evaluate notch detection by selecting the PC or partial cycle button from the tool bar. The drive unit will perform the cycle and complete the calculations. If the notch was detected properly and the window is adequate for a relatively wide range of heart rates, the system is set up correctly and performing to specifications. The user should add appropriate comments and save the partial cycle window to the hard disk with the Save As command from the File menu. Normally, the stop pumping and start pumping functions are not necessary. This is only important if there is a question of the ECG trigger or dicrotic notch settings. Upon performing a partial cycle, the "suggested settings" method can be used to update the patient parameter table, as discussed in Patient Parameter Table.

Drive unit operation should be evaluated on a regular basis using the WinMAV software as a tool. Periodically perform a partial cycle and verify that the dicrotic notch is detected properly and the window for detection is adequate.

EXAMPLE WAVEFORM

In an example of a partial cycle where the dicrotic notch was detected in the animal model, the window for detection is very wide (as shown by the bar on the second trace), allowing for dicrotic notch detection under a wide range of heart rates. However, this wide a range can also cause problems if noise or artifacts causes a false detection.

This is where the physician must make a decision. When there is no problem detecting the notch given a wide window for detection, this is the best scenario. If detection problems arise, the window should be adjusted to avoid false detections. This may be achieved by limiting the window to a narrower range, forcing detection in this zone. Also notice that the default setting for the notch is slightly later than the actual detected notch. This is a conservative approach that errs on the side of safety. That is, it is better to inflate late rather than early if the notch is not detected.

The entire disclosure of the prior application Ser. No. 60/060,499 filed Sep. 30, 1997, and Ser. No. 60/097,819 filed Aug. 25, 1998 are considered a part of the disclosure of the accompanying application and are hereby incorporated by reference. Additional information regarding the percutaneous access device can be obtained from U.S. Pat. No. 4,634,422 issued Jan. 6, 1987; U.S. Pat. No. 5,242,415 issued Sep. 7, 1993; U.S. Pat. No. 4,913,700 issued Apr. 3, 1990; and Ser. No. 08/856,905 filed May 15, 1997 for a percutaneous access device having a removable turret assembly and are incorporated by reference herein. Additional information regarding the blood pump can be obtained from U.S. Pat. No. 4,630,597 issued Dec. 23, 1986 which is incorporated by reference herein. Additional information regarding the pressure control system and partial cycle blood pressure sensing can be obtained from U.S. patent application Ser. No. 90/036,759 filed Mar. 9, 1998 and U.S. Ser. No. 08/856,904 filed May 15, 1997 which are incorporated by reference herein.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber; and a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient, wherein the control program includes a patient parameter table having physician programmable parameters for modifying cardiac function assistance provided to the patient.

2. The apparatus of claim 1 wherein each of the physician programmable parameters has a predefined default value.

3. The apparatus of claim 1 further comprising:

a software program connectible in electronic communication with the control program for adjusting settings of the drive unit.

4. The apparatus of claim 3 wherein the software program retrieves current values of physician programmable parameters.

5. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber; and a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient, wherein each of the physician programmable parameters is restricted to a value greater than or equal to a predefined minimum value and less than or equal to a predefined maximum value.

6. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber;

a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient; and a software program connectible in electronic communication with the control program for adjusting settings of the drive unit, wherein the software program selectively retrieves a history of the drive unit operation including error detection records.

7. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber;

a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient; and a software program connectible in electronic communication with the control program for adjusting settings of the drive unit, wherein the software program displays a continuous ECG.

8. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber;

a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient; and a software program connectible in electronic communication with the control program for adjusting settings of the drive unit, wherein the software program displays a single-beat sample of aortic pressure waveform obtained in real time from the patient.

9. An apparatus for assisting cardiac function of a patient comprising:

an inflatable chamber operably positionable with respect to an aorta of the patient;

a percutaneous access device implantable with respect to a hypogastric region of the patient and connectible in fluid communication with the inflatable chamber; and a drive unit connectible through the percutaneous access device for selectively inflating and deflating the inflatable chamber in accordance with a control program, the control program for controlling the drive unit in response to a periodically scheduled patient monitoring routine for measuring values of the physiology of the patient, and the control program using measured values as modified in accordance with the control program and physician programmable parameters for assisting cardiac function of the patient, wherein the control program interrupts counterpulsation for two cardiac cycles to perform a partial cycle in order to obtain an aortic pressure waveform, a $Q\text{-}S_2$ interval is measured by the control program from the aortic pressure waveform obtained.

10. The apparatus of claim 9 wherein the control program uses the interval to adjust inflation timing of the blood pump, as modified in accordance with the physician programmable parameters, in response to changes in the heart rate and hemodynamic state of the patient.

11. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient;

using measured values as modified in accordance with physician programmable parameters for assisting cardiac function of the patient; and providing a patient parameter table having a plurality of physician programmable parameters for modifying cardiac function assistance provided to the patient.

12. The program of claim 11 wherein each of the physician programmable parameters has a predefined default value.

13. The program of claim 11 further comprising the step of:

adjusting settings of the drive unit with a software program connectible in electronic communication with the drive unit.

14. The program of claim 13 wherein the software program retrieves current values of physician programmable parameters.

15. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient; and using measured values as modified in accordance with physician programmable parameters for assisting cardiac function of the patient, wherein each of the physician programmable parameters is restricted to a value greater than or equal to a predefined minimum value and less than or equal to a predefined maximum value.

16. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient;

using measured values as modified in accordance with physician programmable parameters for assisting cardiac function of the patient; and adjusting settings of the drive unit with a software program connectible in electronic communication with the drive unit, wherein the software program selectively retrieves a history of the drive unit operation including error detection records.

17. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient;

using measured values as modified in accordance with physician programmable parameters for assisting cardiac function of the patient; and adjusting settings of the drive unit with a software program connectible in electronic communication with the drive unit, wherein the software program displays a continuous ECG.

18. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient;

using measured values as modified in accordance with physician programmable parameters for assisting cardiac function of the patient; and adjusting settings of the drive unit with a software program connectible in electronic communication with the drive unit, wherein the software program displays a single-beat sample of aortic pressure waveform obtained in real time from the patient.

19. A control program for assisting cardiac function during a cardiac cycle of a patient having a cardiac assist device with drive unit connectible to an inflatable chamber operatively positionable with respect to an aorta of the patient comprising the steps of:

automatically controlling the drive unit in response to a periodically scheduled patient monitoring routine for measuring values of physiology of the patient;

using measured values as modified in accordance with physician programmable parameters for assisting cardiac function of the patient;

interrupting counterpulsation for two cardiac cycles to perform a partial cycle in order to obtain an aortic pressure waveform; and measuring a $Q-S_2$ interval from the aortic pressure waveform obtained.

20. The program of claim 19 further comprising the step of:

using the measured $Q-S_2$ interval to adjust inflation timing of the blood pump, as modified in accordance with the physician programmable parameters, in response to changes in the heart rate and hemodynamic state of the patient.

* * * * *